United States Patent
Yoshiyama et al.

(10) Patent No.: US 7,683,106 B2
(45) Date of Patent: Mar. 23, 2010

(54) PRIMER FOR DENTAL MATERIALS AND PULP CAPPING AGENT FOR DENTIN REGENERATION

(75) Inventors: Masahiro Yoshiyama, Okayama (JP); Yoshihiro Nishitani, Okayama (JP); Sadami Tsutsumi, Kyoto (JP); Suong-Hyu Hyon, Uji (JP)

(73) Assignee: Nippon Synthetic Chemical Industry Co., Ltd. (JP)

( * ) Notice: Subject to any disclaimer, the term of this patent is extended or adjusted under 35 U.S.C. 154(b) by 680 days.

(21) Appl. No.: 10/548,374

(22) PCT Filed: Mar. 5, 2004

(86) PCT No.: PCT/JP2004/002848

§ 371 (c)(1),
(2), (4) Date: May 25, 2006

(87) PCT Pub. No.: WO2004/078148

PCT Pub. Date: Sep. 16, 2004

(65) Prior Publication Data

US 2006/0252846 A1 Nov. 9, 2006

(30) Foreign Application Priority Data

Mar. 7, 2003 (JP) .............................. 2003-060845
Mar. 26, 2003 (JP) .............................. 2003-084443

(51) Int. Cl.
*A61K 6/08* (2006.01)
*C08K 3/38* (2006.01)

(52) U.S. Cl. ........................ 523/114; 523/118; 523/200; 524/405; 527/200; 527/207

(58) Field of Classification Search ................. 523/114, 523/118; 527/200, 207; 524/405
See application file for complete search history.

(56) References Cited

U.S. PATENT DOCUMENTS 5,373,034 A * 12/1994 Wang et al. .................. 523/118
6,649,669 B2 * 11/2003 Dickens ....................... 522/76

FOREIGN PATENT DOCUMENTS

| | | |
|---|---|---|
| JP | 57-34148 | 2/1982 |
| JP | 57-59940 | 4/1982 |
| JP | 60-144304 | 7/1985 |
| JP | 2-156954 | 6/1990 |
| JP | 4-351642 | 12/1992 |
| JP | 06-256132 | 9/1994 |
| JP | 6-340555 | 12/1994 |
| JP | 9-175921 | 7/1997 |
| JP | 10-216219 | 8/1998 |
| JP | 10-243996 | 9/1998 |
| JP | 2000-316879 | 11/2000 |
| JP | 2002-29909 | 1/2002 |
| JP | 2002-363084 | 12/2002 |

OTHER PUBLICATIONS

K. Matsumura, et al.., Ethylene-Vinylalcohol Kyojugotai to Titanium tono Secchaku, Secchaku, 2002, vol. 46, No. 11, pp. 501 to 505.

K. Matsumura, et al., Shikon Maku o Yusuru Jinko Shikon no Kaihatsu, The Journal of the Japanese Society for Dental Materials and Devices, 200, vol. 19, No. 4, pp. 361 to 366.

T, Sato, et al. Zogeshitsu Saisekkaika to Shizui Saibo kara Zogega Saibo eno Bunka, the Quitessence, Jan. 10, 2003, vol. 22, No. 1, pp. 216-219.

International Search Report for PCT/JP2004/002848, mailed Apr. 27, 2004, 2 pages.

K. Matsumura, et al., Shikon Maku o Yusuru Jinko Shikon no Kaihatsu, The Journal of the Japanese Society for Dental Materials and Devices, vol. 19, No. 4, pp. 361 to 366, 2000.

* cited by examiner

*Primary Examiner*—Tae H Yoon
(74) *Attorney, Agent, or Firm*—Antonelli, Terry, Stout & Kraus, LLP.

(57) ABSTRACT

A dental material primer and a dentin-regenerating pulp-capping agent which exhibit an excellent dentin-regenerating action, are disclosed. The dental material primer includes a hydrolyzed ethylene-vinyl acetate copolymer in which collagen is immobilized and the dentin-regenerating pulp-capping agent includes a hydrolyzed ethylene-vinyl acetate copolymer, in which collagen is immobilized, and a binder.

8 Claims, No Drawings

PRIMER FOR DENTAL MATERIALS AND PULP CAPPING AGENT FOR DENTIN REGENERATION

RELATED APPLICATION

This application is a U.S. national stage filing under 35 U.S.C. §371 of International Application No. PCT/JP2004/002848 filed Mar. 5, 2004 and claiming priority of Japanese Patent Application No. 2003-060845 filed Mar. 7, 2003 and Japanese Patent Application No. 2003-084443 filed Mar. 26, 2003.

TECHNICAL FIELD

The present invention relates to a dental material primer having dentin-regenerating ability which is used for treatment of a decayed tooth, and a dentin-regenerating pulp-capping agent.

BACKGROUND ART

In the treatment of a decayed tooth, there has been conventionally carried out a treatment method of ablating a carries portion of an enamel or dentin and burying a metal, a resin or the like in the portion. In this bout, the dental pulp is occasionally exposed at a portion which the dentin was removed.

In this case, when the dental pulp portion is directly covered with a metal or a resin, microbes enter into a gap between the dental pulp and the metal or the resin to cause inflammation since an adhesive force between the dental pulp and the metal or the resin may be insufficient, and pain is also occasionally felt against slight stimulation. Therefore, it is desirable that the dental pulp is capped with regenerated dentin.

In the treatment of a decayed tooth, there has been conventionally carried out a treatment method of ablating an caries portion of an enamel or dentin and burying a metal, a resin or the like in the portion. In this bout, the dental pulp is occasionally exposed at a portion which the dentin was removed.

In this case, when the dental pulp portion is directly covered with a metal or a resin, microbes enters into a gap between the dental pulp and the metal or the resin to cause inflammation since an adhesive force between the dental pulp and the metal or the resin may be insufficient, and pain is also occasionally felt against slight stimulation. Therefore, it is desirable that the dental pulp is capped with regenerated dentin.

As the regenerating method of the dentin, a calcium hydroxide preparation is occasionally used as a pulp-capping agent for the exposed dental pulp. However, a necrotic layer by strong alkali is generated on the dental pulp face which is brought in contact with calcium hydroxide, and even if the dentin is occasionally regenerated at its lower portion, its regenerating rate is considered to be very low. Additionally, since the dental pulp backs downward often by the necrosis, it is not preferable.

Recently, various investigations for studying an effective component as a pulp-capping agent for treatment of promoting the regeneration of the dentin in place of the calcium hydroxide preparation have been carried out. For example, there are proposed a pulp-capping agent containing polysaccharides such as N-acetyl-D-glucoseamine in Japanese Unexamined Patent Publication No. 6-256132, a dentin forming pulp-capping agent containing bone morphogenetic protein as an effective component in Japanese Unexamined Patent Publication No. 6-340555 and a secondary dentin forming promoter containing the blood extract of a cow in Japanese Unexamined Patent Publication No. 2002-363084. However, the regeneration effect of the dentin can be expected to a certain degree by the pulp-capping agents and promoters described in these patent references, but it cannot be said that sufficient study is carried out for a foothold of regeneration which is important at regenerating, namely, for the foothold of cells having ability of regenerating the dentin. One factor for insufficient regeneration effect is considered that the foothold for proliferating cells having ability of regenerating the dentin to promote regeneration of the dentin excellently is not adequately secured.

Further, it is said that the dental pulp portion is preferably subjected to primer treatment and, then, is covered with a pulp-capping agent. As the dental primer, a primer containing specific particles is proposed in Japanese Unexamined Patent Publication No. 9-175921. However, since the dental primer described in the patent reference contains polymerizable monomers containing an acid group such as a phosphoric acid group, a carboxylic acid group, a sulfonic acid group or a phosphonic acid group, the regeneration ability of the dentin could not be expected.

DISCLOSURE OF THE INVENTION

The present invention relates to a dental material primer and a dentin-regenerating pulp-capping agent which exhibit excellent dentin regeneration action and are very useful in a biological direct pulp capping in dental treatment.

Namely, the present invention relates to a dental material primer comprising a hydrolyzed ethylene-vinyl acetate copolymer in which collagen is immobilized.

The hydrolyzed ethylene-vinyl acetate copolymer in which collagen is immobilized is preferably fine particles having a mean particle size of 0.2 μm to 30 μm.

The amount of the hydrolyzed ethylene-vinyl acetate copolymer in which collagen is immobilized collagen is preferably 1 to 50% by weight.

The dental material primer preferably contains a boron compound in an amount of 0.001 to 0.1 part by weight of converted to boron content based on 100 parts by weight of the hydrolyzed ethylene-vinyl acetate copolymer in which collagen is immobilized.

The dental material primer preferably contains a hydroxyl group-containing polymerizable monomer or an acidic group-containing polymerizable monomer as a primer component.

The present invention also relates to a dentin-regenerating pulp-capping agent comprising a hydrolyzed ethylene-vinyl acetate copolymer in which collagen is immobilized and a binder.

The hydrolyzed ethylene-vinyl acetate copolymer in which collagen is immobilized is preferably fine particles having a mean particle size of 0.2 μm to 30 μm.

The dentin-regenerating pulp-capping agent preferably contains 1 to 100 parts by weight of the hydrolyzed ethylene-vinyl acetate copolymer in which collagen is immobilized based on 100 parts by weight of the binder.

The dentin-regenerating pulp-capping agent preferably contains a boron compound in an amount of 0.001 to 0.1 part by weight converted to boron content based on 100 parts by weight of the hydrolyzed ethylene-vinyl acetate copolymer in which collagen is immobilized.

The binder preferably comprises a photo-curable monomer.

BEST MODE FOR CARRYING OUT THE INVENTION

First of all, the dental material primer of the present invention will be explained.

The hydrolyzed ethylene-vinyl acetate copolymer in which collagen is immobilized in the present invention is not particularly limited, but the amount of ethylene is preferably 5 to 60% by mol, more preferably 10 to 50% by mol, further preferably 20 to 45% by mol, and particularly preferably 25 to 40% by mol. When the amount of ethylene is less than 5% by mol, stability within an organism is deteriorated and, adversely, when it exceeds 60% by mol, it is not preferable since the immobilization rate of collagen is deteriorated.

Also, the hydrolysis degree of a vinyl acetate component is preferably at least 85% by mol, more preferably at least 90% by mol, further preferably at least 95% by mol, and particularly preferably at least 99% by mol. When the hydrolysis degree is less than 85% by mol, it is not preferable since the immobilization rate of collagen is deteriorated.

Further, the average polymerization degree (which is calculated from number average molecular weight (polystyrene conversion) when the ethylene-vinyl acetate copolymer after reacetification is measured with GPC in which tetrahydrofuran is an eluant) of an hydrolyzed ethylene-vinyl acetate copolymer is preferably 100 to 1000, more preferably 200 to 800, and particularly preferably 300 to 700. When the average polymerization degree is less than 100, it is not preferable since stability within an organism is deteriorated and, adversely, when it exceeds 1000, it is not preferable since granulation of the hydrolyzed ethylene-vinyl acetate copolymer described later to be fine particles becomes difficult.

The above-mentioned hydrolyzed ethylene-vinyl acetate copolymer may be copolymerized with a copolymerizable ethylenically unsaturated monomer within a range which does not trespass objects of the present invention. Examples of such a monomer are: olefins such as propylene, 1-butene and isobutene; unsaturated acids, salts thereof or mono or dialkyl esters having 1 to 18 carbon atoms thereof such as acrylic acid, methacrylic acid, crotonic acid, phthalic acid (and its anhydride), maleic acid (and its anhydride) and itaconic acid (and its anhydride); acrylamides such as acrylamide, N-alkylacrylamide having 1 to 18 carbon atoms, N,N-dimethylacryl amide, 2-acrylamide propane sulfonic acid or a salt thereof, and acryl amidepropyldimethylamine or a salt thereof or a quaternary salt thereof; methacrylamides such as methacrylamide, N-alkylmethacryl amide having 1 to 18 carbon atoms, N,N-dimethylmethacryl amide, 2-methacrylamide propane sulfonic acid or a salt thereof, and methacrylamide propyldimethylamine or a salt thereof or a quaternary salt thereof; N-vinylamides such as N-vinylpyrrolidone, N-vinylformamide and N-vinylacetamide; vinylcyanides such as acrylonitrile and methacrylonitrile; vinyl ethers such as alkyl vinyl ether having 1 to 18 carbon atoms, hydroxyalkyl vinyl ether and alkoxyalkyl vinyl ether; halogenated vinyls such as vinyl chloride, vinylidene chloride, vinyl fluoride, vinylidene fluoride and vinyl bromide; allyl acetate, allyl chloride, allyl alcohol, dimethylallyl alcohol, trimethyl-(3-acrylamide-3-dimethylpropyl)-ammonium chloride, acrylamide-2-methylpropanesulfonic acid.

Also, post modification such as urethanation, acetalization and cyanoethylation may be carried out within a range not impairing objects of the present invention. Further, the hydrolyzed ethylene-vinyl acetate copolymer containing silicon can be also used as described in Japanese Unexamined Patent Publication No. 60-144304.

The hydrolyzed ethylene-vinyl acetate copolymer is preferably fine particles having a mean particle size of 0.2 μm to 30 μm, more preferably 0.5 μm to 10 μm, and particularly preferably 0.8 μm to 5 μm. When the particle size is less than 0.2μm, it is not preferable since the immobilization rate of collagen is lowered and, adversely, when it exceeds 30 μm, it is not preferable since homogeneous cell growth may not be carried out.

The hydrolyzed ethylene-vinyl acetate copolymer in the form of fine particles can be obtained by a process of spray drying after pulverizing pellet products and granulates industrially prepared by a low temperature pulverization process or a wet pulverization process, a process of spray drying an emulsion obtained by cooling a water- alcohol solution or by adding a poor solvent and the like.

Collagen can be immobilized on the fine particles of hydrolyzed ethylene-vinyl acetate copolymer obtained above. When the collagen is immobilized, firstly, it is necessary that carboxyl groups are introduced on the surface of the hydrolyzed ethylene-vinyl acetate copolymer by oxidizing.

When the carboxyl groups are introduced, an oxidation process using ozone can be adopted. The oxidation process is excellent from viewpoints that an oxidizing agent does not remain as impurities or foreign compounds in the hydrolyzed ethylene-vinyl acetate copolymer or an organism, it is simple and those having three-dimensional shape can be also uniformly oxidized. Specifically, it can be introduced by carrying out gas treatment of the fine particles of the hydrolyzed ethylene-vinyl acetate copolymer in a hot water bath using an ozone generating device. The amount of the introduced carboxyl group is preferably 0.01 μmol·cm$^{-2}$ to 2 μmol·cm$^{-2}$, and more preferably 0.05 μmol·cm$^{-2}$ to 1.5 μmol·cm$^{-2}$.

Then, collagen is immobilized on the hydrolyzed ethylene-vinyl acetate copolymer having a surface to which the carboxyl group has been introduced. Any one of commercially available types I to V can be used as collagen. The immobilization of collagen is carried out by immersing the fine particles of the hydrolyzed ethylene-vinyl acetate copolymer to which the carboxyl group was introduced, into the phosphoric acid solution of collagen. Collagen can be immobilized by ionic adsorption on the surface of the fine particles of the hydrolyzed ethylene-vinyl acetate copolymer.

The immobilization amount of collagen at this time is not particularly limited, but is preferably at least 5 μg·cm$^{-2}$, more preferably at least 10 μg·cm$^{-2}$, and particularly preferably at least 16 μg·cm$^{-2}$. When the immobilization amount is less than 5 μg·cm$^{-2}$, it is not preferable because the adhesion efficiency of cells having ability of regenerating the dentin is lowered and the regeneration effect of the dentin is occasionally scarce. Further, the upper limit of the immobilization amount of collagen is not particularly specified, but the immobilization amount of collagen is proportional to the amount of the carboxyl group introduced on the surface of the hydrolyzed ethylene-vinyl acetate copolymer. It is not preferable that the introduction amount of the carboxyl group exceeds a suitable amount considering the durability of the fine particles of the hydrolyzed ethylene-vinyl acetate copolymer, namely, the upper limit of the immobilization amount of collagen is about 40 μg·cm$^{-2}$ and, further about 35 μg·cm$^{-2}$.

In the present invention, it is preferable that a boron compound is previously contained in the above-mentioned hydrolyzed ethylene-vinyl acetate copolymer. Examples of the boron compound are boric acid, calcium borate, cobalt borate, zinc borate (such as zinc tetraborate, zinc metaborate), aluminum potassium borate, ammonium borate (such as ammonium metaborate, ammonium tetraborate, ammonium pentaborate, ammonium octaborate), cadmium borate (such as cadmium orthoborate, cadmium tetraborate), potassium borate (such as potassium metaborate, potassium tetraborate, potassium pentaborate, potassium hexaborate, potassium octaborate), silver borate (such as silver metaborate, silver tetraborate), copper borate (such as copper (II) borate, copper metaborate, copper tetraborate), sodium borate (such as sodium metaborate, sodium diborate, sodium tetraborate, sodium pentaborate, sodium hexaborate, sodium octaborate), lead borate (such as lead metaborate, lead hexaborate), nickel borate (such as nickel orthoborate, nickel diborate, nickel tetraborate, nickel octaborate), barium borate (such as barium orthoborate, barium metaborate, barium diborate, barium tetraborate), bismuth borate, magnesium borate (such as magnesium orthoborate, magnesium diborate, magnesium metaborate, trimagnesium tetraborate, pentamagnesium tetraborate), manganese borate (such as manganous borate, manganese metaborate, manganese tetraborate), lithium borate (such as lithium metaborate, lithium tetraborate, lithium pentaborate), additionally, borate minerals such as borax, Kernite, Inyoite, Kotoite, Suanite and Szaibelyite, and the like. Borax, boric acid and sodium borate (such as sodium metaborate, sodium diborate, sodium tetraborate, sodium pentaborate, sodium hexaborate, sodium octaborate) are preferably used.

The amount of the boron compound is not particularly limited, but is preferably 0.001 to 0.1 part by weight, and more preferably 0.01 to 0.07 part by weight converted to boron content based on 100 parts by weight of the hydrolyzed ethylene-vinyl acetate copolymer. When the amount is smaller than 0.001 part by weight, the durability of the primer may be lowered and, adversely, when it is more than 0.1 part by weight, the effect of the present invention may not be exhibited sufficiently and it is not preferable.

When the boron compound is contained in the hydrolyzed ethylene-vinyl acetate copolymer, it can be contained by bringing the hydrolyzed ethylene-vinyl acetate copolymer in contact with the aqueous solution of the boron compound.

The process of bringing the hydrolyzed ethylene-vinyl acetate copolymer in contact with the aqueous solution of the boron compound is not particularly limited, but it is preferable that, usually, the above-mentioned boron compound is contained by charging the hydrolyzed ethylene-vinyl acetate copolymer molded into a pellet shape in the aqueous solution and agitating.

The dental material primer of the present invention comprises the hydrolyzed ethylene-vinyl acetate copolymer in which collagen is immobilized as described above. As other primer component, a commercially available primer component for dentistry can be used. Examples of the primer component are a hydroxyl group-containing polymerizable monomer, an acidic group-containing polymerizable monomer, and the like.

Examples of the hydroxyl group-containing polymerizable monomer are hydroxyl group-containing (meth)acrylates such as 2-hydroxyethyl(meth)acrylate, 2- or 3-hydroxypropyl(meth)acrylate, 4-hydroxybutyl(meth)acrylate, 5-hydroxypentyl(meth)acrylate, 6-hydroxyhexyl(meth)acrylate, 10-hydroxydecyl(meth)acrylate, 1,2- or 1,3- and 2,3-dihydroxypropane(meth)acrylate, diethyleneglycol mono(meth)acrylate, triethyleneglycol mono(meth)acrylate, tetraethyleneglycol mono(meth)acrylate, pentaethyleneglycol mono(meth)acrylate, polyethyleneglycol mono(meth)acrylate, dipropyleneglycol mono(meth)acrylate and polypropyleneglycol mono(meth)acrylate; hydroxyl group-containing (meth)acryl amides such as N-methylol(meth)acryl amide, N-(2-hydroxyethyl)(meth)acryl amide, N-(3-hydroxypropyl)(meth)acryl amide, N-(4-hydroxybutyl)(meth)acryl amide, N-(5-hydroxypentyl)(meth)acryl amide, N-(6-hydroxyhexyl)(meth)acryl amide, N-(10-hydroxydecyl)(meth)acryl amide, N-(meth)acryloyl-1,2-dihydroxypropylamine, N-(meth)acryloyl-1,3-dihydroxypropylamine and N-(meth)acryloyl-2,3-dihydroxypropylamine; an addition product of aliphatic or aromatic polyol (including phenol) with glycidyl (meth)acrylates (GMA), such as 2-hydroxy-3-phenoxypropyl(meth)acrylate, 2-hydroxy-3-naphthoxypropyl(meth)acrylate and bisphenol A diglycidyl(meth)acrylate.

Examples of the acidic group-containing polymerizable monomer are a polymerizable monomer containing a carboxylic group, a monomer containing a phosphoric acid group and a monomer containing a sulfonic acid group.

Examples of the monomer containing a carboxylic group are (meth)acryl acid, maleic acid, p-vinylbenzoic acid, 11-(meth)acryloyloxy-1,1-undecanedicarboxylic acid, 2-(meth)acryloyloxyethyl-3'-methacryloyloxy-2'-(3,4-dicarboxybenzoyloxy)propyl succinate, 2-(meth)acryloyloxyethylhydrogen maleate, 2-(meth)acryloyloxyethylhydrogen succinate, 2-(meth)acryloyloxyethylhydrogen phthalate, 3-(meth)acryloyloxypropylhydrogen maleate, 3-(meth)acryloyloxypropylhydrogen succinate, 1,4-di(meth)acryloyloxymethylpyromellitic acid, 6-(meth)acryloyloxyethylnaphthalene-1,2,6-tricarboxylic acid, 4-(meth)acryloyloxymethyl trimellitic acid and anhydride thereof, 4-(meth)acryloyloxyethyl trimellitic acid and anhydride thereof, 4-(meth)acryloyloxybutyl trimellitic acid and anhydride thereof, 4-[2-hydroxy-3-(meth)acryloyloxy]butyl trimellitic acid and anhydride thereof, 2,3-bis(3,4-dicarboxybenzoyloxy)propyl(meth)acrylate, N,O-di(meth)acryloyloxy tyrosine, O-(meth)acryloyloxy tyrosine, N-(meth)acryloyloxy alanine, N-(meth)acryloyloxy glycine, N-(meth)acryloyloxy tyrosine, N-(meth)acryloyl-p-aminobenzoic acid, N-(meth)acryloyl-O-aminobenzoic acid, N-(meth)acryloyl-5-aminosalicylic acid, N-(meth)acryloyl-4-aminosalicylic acid, 2- or 3- or 4-(meth)acryloyloxybenzoic acid, an addition product of 2-hydroxyethyl(meth)acrylate with trimellitic acid dianhydride, 2-(3,4-dicarboxybenzoyloxy)-1,3-di(meth)acryloyloxypropane, 4-[(2-hydroxy-3-(meth)acryloyloxypropyl)amino]phthalic acid and 3- or 4-[N-methyl-N-(2-hydroxy-3-(meth)acryloyloxypropyl)amino] phthalic acid.

Examples of the polymerizable monomer containing a phosphoric acid group are 2-(meth)acryloyloxyethyldihydrogen phosphate, 2-(meth)acryloyloxyethyl acid phosphate, 2- and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyldihydrogen phosphate, 12-(meth)acryloyloxydodecyl acid phosphate, bis[2-(meth)acryloyloxyethyl] acid phosphate, bis[2- or 3-(meth)acryloyloxypropyl] acid phosphate, bis[2-(meth)acryloyloxyethyl] hydrogen phosphate, 2-(meth)acryloyloxyethylphenyl acid phosphate, and 2-(meth)acryloyloxyethyl-p-methoxyphenyl acid phosphate. The phosphoric acid group in these compounds can be replaced with a thiophosphoric acid group.

Further, examples of the polymerizable monomer containing a sulfonic acid group are 2-sulfoethyl(meth)acrylate, 2-methyl-2-(meth)acrylamidepropane sulfonic acid, 2- or 1-sulfo-1- or 2-propyl(meth)acrylate, 1- or 3-sulfo-2-butyl (meth)acrylate, 3-bromo-2-sulfo-2-propyl(meth)acrylate, 3-methoxy-1-sulfo-2-propyl(meth)acrylate, 1,1-dimethyl-2- sulfoethyl(meth)acryl amide and 3-methoxy-1-sulfo-2-propyl(meth)acrylate and a typical example of sulfonic acid is vinyl sulfonic acid.

These polymerizable monomers may be used alone or in combination of at least two kinds.

Further, a polymerization initiator can be used in combination with the above-mentioned primer component, if necessary. Examples of the polymerization initiator are a thermal-polymerization initiator and a photo-polymerization initiator.

Examples of the thermal-polymerization initiator are: peroxides such as benzoyl peroxide, p-chlorobenzoyl peroxide, tert-butylperoxy-2-ethylhexanoate, tert-butylperoxy dicarbonate, and diisopropylperoxy dicarbonate; azo compounds such as azobisisobutyronitrile; boron compounds such as tributylborane, a partially oxidized compound of tributylborane, sodium tetraphenylborate, sodium tetrakis(p-fluorophenyl)borate and triethanolamine tetraphenylborate; barbituric acids such as 5-butylbarbituric acid and 1-benzyl-5-phenylbarbituric acid; and sulfinates such as sodium benzenesulfinate and sodium p-toluenesulfinate.

Also, examples of the photo-polymerization initiator are: benzoin alkyl ethers such as benzoin methyl ether, benzoin ethyl ether and benzoin isopropyl ether; benzyl ketals such as benzyldimethyl ketal and benzyldiethyl ketal; benzophenones such as benzophenone, 4,4'-dimethylbenzophenone and 4-methacryloxybenzophenone; α-diketones such as diacetyl, 2,3-pentadionebenzyl, camphorquinone, 9,10-phenanthraquinone and 9,10-anthraquinone; thioxanthone compounds such as 2,4-diethoxythioxanthone, 2-chlorothioxanthone and methylthioxanthone; and bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide and bis-(2,4,6-trimethylbenzoyl)-phenylphosphine oxide.

Further, with the photo-polymerization initiator, reducing agents tertiary amines such as 2-(dimethylamino)ethyl(meth)acrylate, ethyl 4-dimethylaminobenzoate, N-methyldiethanolamine, aldehydes such as laurylaldehyde, dimethylaminobenzaldehyde and terephthalaldehyde, and sulfur-containing compounds such as 2-mercaptobenzoxazole, 1-decanethiol, thiosalicylic acid and thiobenzoic acid are occasionally in a combination use.

The amount of the hydrolyzed ethylene-vinyl acetate copolymer in which collagen is immobilized in the dental material primer of the present invention is not particularly limited, but is preferably 1 to 50% by weight in the primer, more preferably 5 to 30% by weight, and particularly preferably 8 to 15% by weight. When the amount is less than 1% by weight, it is not preferable since the functional effect of the present invention becomes poor and, adversely, when it exceeds 50% by weight, it is not preferable since the adhesive properties of an adhesive used on the primer may be lowered.

When the dental material primer of the present invention is applied to treatment for the decayed tooth, it can be used in the same manner as a conventional dental material primer. For example, after the dental caries portion is ablated, the surface of the ablated dental caries portion is sterilized and disinfected with sodium hypochlorite, hydrogen peroxide solution and the like, the primer of the present invention is coated and a commercially available adhesive for dentistry is filled, then, the primer is cured by irradiating ultraviolet rays by a high pressure, middle pressure or low pressure mercury lamp, visible light by a halogen lamp, a xenon lamp and a metal halide lamp.

The dental adhesive is not particularly limited, but a polymerizable monomer for dentistry, preferably, a photo-curable monomer can be used. Examples of the polymerizable monomer for dentistry are polymerizable monomers having a (meth)acryloyl group, such as a monofunctional vinyl monomer, a difunctional vinyl monomer and a trifunctional vinyl monomer.

Examples of the monofunctional vinyl monomer are: methacrylates such as methyl methacrylate, ethyl methacrylate, isopropyl methacrylate, hydroxyethyl methacrylate, tetrahydrofurfuryl methacrylate and glycidyl methacrylate; and acrylates corresponding to these methacrylates; acrylic acid, methacrylic acid, p-methacryloyloxybenzoic acid, N-2-hydroxy-3-methacryloyloxypropyl-N-phenylglycin, 4-methacryloyloxyethyltrimellitic acid and anhydride thereof, 6-methacryloyloxyhexamethylenemalonic acid, 10-methacryloyloxydecamethylenemalonic acid, 2-methacryloyloxyethyldihydrogen phosphate, 10-methacryloyloxydecyldihydrogen phosphate, and 2-hydroxyethylhydrogenphenyl phosphonate.

Examples of the difunctional vinyl monomer are: aromatic compounds such as 2,2-bis(methacryloyloxyphenyl)propane, 2,2-bis[4-(3-methacryloyloxy)-2-hydroxypropoxyphenyl]propane, 2,2-bis(4-methacryloyloxyphenyl) propane, 2,2-bis(4-methacryloyloxypolyethoxyphenyl) propane, 2,2-bis(4-methacryloyloxydiethoxyphenyl) propane, 2,2-bis(4-methacryloyloxytetraethoxyphenyl) propane, 2,2-bis(4-methacryloyloxypentaethoxyphenyl) propane, 2,2-bis(4-methacryloyloxydipropoxyphenyl) propane, 2-(4-methacryloyloxydiethoxyphenyl)-2-(4-methacryloyloxydiethoxyphenyl)propane, 2-(4-methacryloyloxydiethoxyphenyl)-2-(4-methacryloyloxytriethoxyphenyl)propane, 2-(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, and acrylates corresponding to these methacrylates; diadducts (urethane diacrylate and the like) which are obtained by addition of vinyl monomers having a —OH group such as methacrylates such as 2-hydroxyethyl methacrylate, 2-hydroxypropyl methacrylate and 3-chloro-2-hydroxypropyl methacrylate, or acrylates corresponding to these methacrylates, with diisocyanate compounds having an aromatic group such as methylbenzene diisocyanate and 4,4'-diphenylmethane diisocyanate.

Further, examples of the difunctional vinyl monomer include: aliphatic compounds such as ethyleneglycol dimethacrylate, diethyleneglycol dimethacrylate, triethyleneglycol dimethacrylate, butyleneglycol dimethacrylate, neopentylglycol dimethacrylate, propyleneglycol dimethacrylate, 1,3-butanediol dimethacrylate, 1,4-butanediol dimethacrylate and 1,6-hexanediol dimethacrylate, and acrylates corresponding to these methacrylates; diadducts which are obtained by addition of vinyl monomers having a —OH group such as methacrylates such as 2-hydroxyethyl methacrylate, 2-hydroxypropyl methacrylate and 3-chloro-2-hydroxypropyl methacrylate, or acrylates corresponding to these methacrylates, with diisocyanate compounds such as hexamethylene diisocyanate, trimethylhexamethylene diisocyanate, diisocyanatemethylcyclohexane, isophorone diisocyanate and methylenebis(4-cyclohexylisocyanate); acrylic anhydride, methacrylic anhydride, 1,2-bis(3-methacryloyloxy-2-hydroxypropoxy)ethyl, di(2-methacryloyloxypropyl) phosphate.

Also, examples of the trifunctional vinyl monomer are methacrylates such as trimethylolpropane trimethacrylate, trimethylolethane trimethacrylate, pentaerythrytol trimethacrylate and trimethylolmethane trimethacrylate, and acrylates corresponding to these methacrylates. Examples of the tetrafunctional vinyl monomer include pentaerythrytol tetramethacrylate, pentaerythrytol tetraacrylate, and diadducts which are obtained by addition of glycidol dimethacrylate, with diisocyanate compounds such as diisocyanate methylbenzene, diisocyanate methylcyclohexane, isophorone diisocyanate, hexamethylene diisocyanate, trimethylhexamethylene diisocyanate, methylenebis(4-cyclohexyl isocyanate), 4,4'-diphenylmethane diisocyanate and tolylene-2,4-diisocyanate.

These polymerizable monomers may be used alone or in combination of at least two kinds.

Also, a polymerization initiator functioning by heat or light can be used in combination, if necessary, and as the polymerization initiator, those described above as being used in combination with the primer component can be used.

Also, fillers may be compounded in the dental adhesive. Examples of the filler are inorganic fillers such as silica, silica-alumina, alumina, alumina-quartz, glass, zirconia, kaoline, clay, synthetic zeolite, calcium phosphate, barium sulfate and titanium oxide; and organic fillers such as polymethyl methacrylate powder. Further, organic-inorganic complex fillers obtained by coating the surface of the above-mentioned inorganic fillers by polymerization with the polymerizable monomer, or by suspension polymerization of the polymerizable monomer in the presence of inorganic fillers are also used.

The particle size of these fillers is at most 100 μm and usually at most 30 μm, and fine fillers having a particle size of 10 μm to 50 μm are also used. Further, the surface of the inorganic fillers may be previously treated with a silane coupling agent and the like to be hydrophilic or hydrophobic.

Examples of commercially available dental adhesives are specifically CLEARFIL MEGABOND (available from Kuraray Medical Inc.), AQ BOND (available from Sunmedical, Inc.), SINGLE BOND (available from 3M Health Care Limited).

In the present invention, since the primer is equipped with function as a pulp-capping agent, the application of the pulp-capping agent on the adhesive is not always required. But the dentin-regenerating pulp-capping agent of the present invention or a commercially available pulp-capping agent can be also used.

Then, treatment for decayed tooth is completed by filling a composite resin on the dental adhesive.

Fillers are compounded with the composite resin for the purpose of improving mechanical strength, and the fillers described above as being compoundable in the dental adhesive can be used.

Further, as the polymerizable monomer used as the composite resin, those which are generally used for dental composite materials can be used. The most typical polymerizable monomer is a polymerizable monomer having an acryl group and/or a methacryl group. Specific examples thereof are an addition product of bisphenol A glycidyl methacrylate adduct, 2,2-bis(4-(methacryloxyethoxy)phenyl)propane, 2,2-bis(4-(methacryloxydiethoxy)phenyl)propane, ethyleneglycol dimethacrylate, triethyleneglycol dimethacrylate, urethane dimethacrylate, tetrafunctional urethane methacrylate, hexafunctional urethane methacrylate, trimethylolpropane trimethacrylate, methyl methacrylate and lauryl methacrylate.

The above-mentioned filler is usually compounded in the amount of about 100 to 900 parts by weight based on 100 parts by weight of the polymerizable monomer in the above-described composite resin.

Further, known additives such as a pigment and a polymerization inhibitor can be compounded with the composite resin in addition to the above-mentioned fillers.

The composite resin can be cured by irradiating ultraviolet rays by a high pressure, middle pressure or low pressure mercury lamp, visible light by a halogen lamp, a xenon lamp and a metal halide lamp.

In the following, the dentin-regenerating pulp-capping agent of the present invention is explained.

The hydrolyzed ethylene-vinyl acetate copolymer in which collagen is immobilized in the present invention is not particularly limited, but the amount of ethylene is preferably 5 to 60% by mol, more preferably 10 to 50% by mol, further preferably 20 to 45% by mol, and particularly preferably 25 to 40% by mol. When the amount of ethylene is less than 5% by mol, it is not preferable since stability within the organism is decreased and, adversely, when it exceeds 60% by mol, it is not preferable since the immobilization rate of collagen is decreased.

Further, the degree of hydrolysis of the vinyl acetate component is preferably at least 85% by mol, more preferably at least 90% by mol, further preferably at least 95% by mol, and particularly preferably at least 99% by mol. When the degree of hydrolysis is less than 85% by mol, it is not preferable since the immobilization rate of collagen is decreased.

Further, the average polymerization degree (which is calculated from number average molecular weight (polystyrene conversion) when the ethylene-vinyl acetate copolymer after reacetification is measured with GPC in which tetrahydrofuran is an eluent) of the hydrolyzed ethylene-vinyl acetate copolymer is preferably 100 to 1000, more preferably 200 to 800, and particularly preferably 300 to 700. When the average polymerization degree is less than 100, it is not preferable since stability within an organism is decreased and, adversely, when it exceeds 1000, it is not preferable since granulation of the hydrolyzed ethylene-vinyl acetate copolymer described later to be fine particles becomes difficult.

The above-mentioned hydrolyzed ethylene-vinyl acetate copolymer may be copolymerized with a copolymerizable ethylenically unsaturated monomer, within a range which does not trespass objects of the present invention. As the ethylenically unsaturated monomer, those which are described above as the copolymerizable monomer with the hydrolyzed ethylene-vinyl acetate copolymer in the dental material primer of the present invention can be used.

Further, post modification such as urethanation, acetalization and cyanoethylation may be carried out within a range not impairing objects of the present invention. Further, the hydrolyzed ethylene-vinyl acetate copolymer containing silicon can be also used as described in Japanese Unexamined Patent Publication No. 60-144304.

The hydrolyzed ethylene-vinyl acetate copolymer is preferably fine particles having a mean particle size of 0.2 μm to 30 μm, more preferably 0.5 μm to 10 μm, and particularly preferably 0.8 μm to 5 μm. When the particle size is less than 0.2 μm, it is not preferable since the immobilization rate of collagen is lowered and, adversely, when it exceeds 30 μm, it is not preferable since homogeneous cell growth may not be carried out.

The hydrolyzed ethylene-vinyl acetate copolymer in the form of fine particles can be obtained by a process of spray drying after pulverizing pellet products and granulates industrially prepared by a low temperature pulverization process or a wet pulverization process, a process of spray drying an emulsion obtained by cooling an water- alcohol solution or by adding a poor solvent and the like.

Collagen can be immobilized on the fine particles of the hydrolyzed ethylene-vinyl acetate copolymer obtained above. When the collagen is immobilized, firstly, it is necessary that carboxyl groups are introduced on the surface of the hydrolyzed ethylene-vinyl acetate copolymer by oxidizing.

When the carboxyl groups are introduced, an oxidation process using ozone can be adopted. The oxidation process is excellent from viewpoints that an oxidizing agent does not remain as impurities or foreign compounds in the hydrolyzed ethylene-vinyl acetate copolymer or an organism, it is simple and those having three-dimensional shape can be also uniformly oxidized. Specifically, it can be introduced by carrying out gas treatment of the fine particles of the hydrolyzed ethylene-vinyl acetate copolymer in a hot water bath using an ozone generating device. The amount of the carboxyl group to be introduced is preferably 0.01 $\mu mol/cm^{-2}$ to 2 $\mu mol \cdot cm^{-2}$, and more preferably 0.05 $\mu mol \cdot cm^{-2}$ to 1.5 $\mu mol\ cm^{-2}$.

Then, collagen is immobilized on the hydrolyzed ethylene-vinyl acetate copolymer in which the carboxyl group is introduced on the surface thereof. Any one of commercially available types I to V can be used as collagen. The immobilization of collagen is carried out by immersing the fine particles of the hydrolyzed ethylene-vinyl acetate copolymer to which the carboxyl group was introduced, into the phosphoric acid solution of collagen. Collagen can be immobilized by ionic adsorption on the surface of the fine particles of the hydrolyzed ethylene-vinyl acetate copolymer.

The immobilization amount of collagen at this time is not particularly limited, but is preferably at least 5 $\mu g \cdot cm^{-2}$, more preferably at least 10 $\mu g \cdot cm^{-2}$, and particularly preferably at least 16 $\mu g \cdot cm^{-2}$. When the immobilization amount is less than 5 $\mu g \cdot cm^{-2}$, it is not preferable since the adhesion efficiency of cells having ability of regenerating the dentin is lowered and the regeneration effect of the dentin may be scarce. Further, the upper limit of the immobilization amount of collagen is not particularly specified, but the immobilization amount of collagen is proportional to the amount of the carboxyl group introduced on the surface of the hydrolyzed ethylene-vinyl acetate copolymer. When the introduction amount of the carboxyl group is too much, durability of the fine particles is impaired so that the upper limit of the immobilization amount of collagen is about 40 $\mu g \cdot cm^{-2}$ and, further, about 35 $\mu g \cdot cm^{-2}$.

As the binder used for the dentin-regenerating pulp-capping agent of the present invention, those which are described above as the polymerizable monomer for dentistry (preferably a photo-curable monomer) used as a dental adhesive in the dental material primer of the present invention can be used.

Also, a polymerization initiator functioning by heat or light can be used in combination, if necessary, and those which are described above as the polymerization initiator capable of being used in combination with the primer component in the dental material primer of the present invention can be used.

Also, fillers are occasionally compounded in the binder, and as the fillers, those which are described above to be able to compound with the dental adhesive in the dental material primer of the present invention can be used.

The content proportion of the hydrolyzed ethylene-vinyl acetate copolymer to the binder in the dentin-regenerating pulp-capping agent of the present invention is not particularly limited, but the hydrolyzed ethylene-vinyl acetate copolymer is preferably contained in an amount of 1 to 100 parts by weight, more preferably 5 to 50 parts by weight, and particularly preferably 8 to 30 parts by weight based on 100 parts by weight of the binder in the pulp-capping agent. When the amount is less than 1 part by weight, the functional effects of the present invention becomes poor and, adversely, when it exceeds 100 parts by weight, it is not preferable since the adhesive properties and strength of the pulp-capping agent are lowered.

Further, in the dentin-regenerating pulp-capping agent of the present invention, preferably, the hydrolyzed ethylene-vinyl acetate copolymer preliminarily contains a boron compound. As the boron compound, those which are described above as the boron compound capable of being contained in the hydrolyzed ethylene-vinyl acetate copolymer in the dental material primer of the present invention can be used.

The amount of the boron compound is not particularly limited, but is preferably 0.001 to 0.1 part by weight, and more preferably 0.01 to 0.07 part by weight converted to boron content based on 100 parts by weight of the hydrolyzed ethylene-vinyl acetate copolymer. When the amount is smaller than 0.001 part by weight, it is not preferable since durability of the primer may be lowered and, adversely, when it is more than 0.1 part by weight, it is not preferable since the effect of the present invention may not be exhibited sufficiently.

When the boron compound is contained in the hydrolyzed ethylene-vinyl acetate copolymer, it can be contained by bringing the hydrolyzed ethylene-vinyl acetate copolymer in contact with the aqueous solution of the boron compound.

The process of bringing the hydrolyzed ethylene-vinyl acetate copolymer in contact with the aqueous solution of the boron compound is not particularly limited, but it is preferable that the above-mentioned boron compound is usually contained by charging the hydrolyzed ethylene-vinyl acetate copolymer molded into a pellet shape in the aqueous solution and agitating.

When the dentin-regenerating pulp-capping agent of the present invention is applied to treatment for the decayed tooth, after the dental caries portion is ablated, the surface of the ablated dental caries portion is sterilized and disinfected with sodium hypochlorite, hydrogen peroxide solution and the like, treated with the primer for a dental material of the present invention or a commercially available primer for dentistry and coating the pulp-capping agent, then, the primer is cured by irradiating ultraviolet rays by a high pressure, middle pressure or low pressure mercury lamp, visible light by a halogen lamp, a xenon lamp and a metal halide lamp.

Thus, the pulp-capping agent for regenerating dentin is formed by the present invention. And the composite resin is usually filled on the pulp-capping agent for remedy. Fillers are compounded in the composite resin for the purpose of improving mechanical strength and, as the fillers, those which are described above as the fillers being able to compound with a dental adhesive can be used in the dental material primer of the present invention.

Also, as the polymerizable monomer used as the composite resin, those which are described above as the composite resin being able to use in the dental material primer of the present invention can be used.

The fillers are usually compounded in an amount of about 100 to 900 parts by weight based on 100 parts by weight of the polymerizable monomer in the composite resin.

Further, known additives such as a pigment and a polymerization inhibitor can be compounded with the composite resin in addition to the fillers.

The composite resin can be also cured by irradiating ultraviolet rays by a high pressure, middle pressure or low pressure mercury lamp, and visible light by a halogen lamp, a xenon lamp and a metal halide lamp.

Hereinafter, the present invention is explained in detail in examples, but it is not limited thereto. Herein, "parts" and "%" in the examples represent the basis of weight unless otherwise noticed.

EXAMPLE 1

After carboxyl groups were introduced (introduction amount: 0.86 μmol·cm$^{-2}$) on the surface of fine particles of an hydrolyzed ethylene-vinyl acetate copolymer having a mean particle size of 1 μm (amount of ethylene: 29% by mol, hydrolysis degree: 99.7% by mol, average polymerization degree: 450, boric acid: not added) by ozone irradiation, the fine particles were immersed at 25° C. for 16 hours in 0.5% collagen-containing phosphoric acid solution which was prepared by dilution of type I atelocollagen (containing by 0.94% in 5 mM phosphoric acid aqueous solution, pH: 3.7, available from Nitta Gelatin Inc.) derived from commercially available cow with 5 mM phosphoric acid aqueous solution (available from Nacalai Tesque Inc., pH: 3.7) and agitated the solution, and collagen was immobilized on the surface of the fine particles of a hydrolyzed ethylene-vinyl acetate copolymer. The immobilization amount of collagen was 20 μg·cm$^{-2}$.

10 parts of the obtained fine particles of hydrolyzed ethylene-vinyl acetate copolymer in which collagen is immobilized and 90 parts of a commercially available primer (CLEARFIL MEGABOND, available from Kuraray Medical Inc.) were mixed to obtain the dental material primer of the present invention.

Then, the dentin-regenerating experiment below was carried out by using the obtained dental material primer.

Black V class cavities were formed on the maxillomandibular anterior teeth of left and right, premolar teeth and molar teeth for a healthy crab-eating macaque who was 6.6 years after birth and a body weight of 6.6 kg, under general anesthesia, and pulp exposure faces with a diameter of 2 mm were formed at the bottom of central portions. Then, the pulp exposure cavities were divided into two groups (for Example and for Comparative Example), the dental material primer obtained above was coated on one pulp exposure cavity group (for Example), an adhesive (CLEARFIL MEGABOND, available from Kuraray Medical Inc.) was filled on it and cured using a metal halide lamp. Further, a composite resin (CLEARFIL AP-X, available from Kuraray Medical Inc.) was filled on it and cured in the same manner. A similar treatment was carried out for another pulp exposure cavity group (for Comparative Example) except for using only a commercially available primer (CLEARFIL MEGABOND, available from Kuraray Medical Inc.) in place of the dental material primer of the present invention.

The macaque was euthanized after 3 months, the EDTA decalcification (4° C.) of the withdrawal teeth was carried out, thin slice segments were prepared and, then, the formation situation of the regenerated dentin in the pulp exposure cavity group for Example was confirmed with an optical microscope. When a regeneration amount was evaluated with a scanning electron microscope, it was confirmed that no inflammation was observed at the dental pulp portions and the thickness of the regenerated dentin layer was 620 μm.

COMPARATIVE EXAMPLE 1

The pulp exposure cavity group for Comparative Example (the fine particles of a hydrolyzed ethylene-vinyl acetate copolymer in which collagen is immobilized was not added and only an adhesive was used in Example 1) was evaluated, and as a result, it was confirmed that the thickness of the regenerated dentin layer was 360 μm, but inflammation was observed at the dental pulp portions.

EXAMPLE 2

Evaluation was carried out in the same manner except that the fine particles containing the hydrolyzed ethylene-vinyl acetate copolymer having an ethylene amount of 29% by mol, a hydrolysis degree of 99.7% by mol and an average polymerization degree of 450 and the addition amount of boric acid of 0.03 part by weight were used in Example 1. As a result, no inflammation was observed at the dental pulp portions of the pulp exposure cavity group for Example and the thickness of the regenerated dentin layer was 650 μm. Further, the introduction amount of a carboxyl group was 1.30 μmol·cm$^{-2}$ and the immobilization amount of collagen was 30 μg·cm$^{-2}$ at this time.

EXAMPLE 3

Evaluation was carried out in the same manner except that the fine particles containing a hydrolyzed ethylene-vinyl acetate copolymer having an ethylene amount of 29% by mol, a hydrolysis degree of 99.7% by mol and an average polymerization degree of 450 and the addition amount of boric acid of 0.03 part by weight were used and the addition amount of the fine particles was 20 parts in Example 1. As a result, no inflammation was observed at the dental pulp portions of the pulp exposure cavity group for Example and the thickness of the regenerated dentin layer was 680 μm.

EXAMPLE 4

The dentin-regenerating pulp-capping agent of the present invention was obtained by mixing 10 parts of the fine particles obtained in Example 1 of the hydrolyzed ethylene-vinyl acetate copolymer in which collagen is immobilized and 100 parts of an adhesive (CLEARFIL MEGABOND, available from Kuraray Medical Inc.) which was a binder.

Then, a dentin-regenerating experiment below was carried out by using the obtained dentin-regenerating pulp-capping agent.

Black V class cavities were formed on the maxillomandibular canine teeth and molar teeth for five beagles who were 1.6 years after birth, under general anesthesia, and pulp exposure faces with a diameter of 2 mm were formed at the bottom of central portions. Then, the pulp exposure cavities were divided into two groups (for Example and for Comparative Example), a primer (CLEARFIL MEGABOND, available from Kuraray Medical Inc.) was coated on one pulp exposure cavity group (for Example), the pulp-capping agent of the present invention obtained above was coated on it and cured by using a metal halide lamp. Further, a composite resin (CLEARFIL AP-X, available from Kuraray Medical Inc.) was filled on it and cured in the same manner. Similar treatment was carried out for another pulp exposure cavity group (for Comparative Example) except for using a commercially available adhesive (CLEARFIL MEGABOND, available from Kuraray Medical Inc.) in place of the pulp-capping agent of the present invention.

The beagles were euthanized after 3 months, the EDTA decalcification (4° C.) of the withdrawal teeth was carried out, thin slice segments were prepared, and then the formation situation of the regenerated dentin in the pulp exposure cavity group for Examples was confirmed with an optical microscope. When a regeneration amount was evaluated with a scanning electron microscope, it was confirmed that inflammation was hardly observed at the dental pulp portions and the thickness of the regenerated dentin layer was 500 µm.

COMPARATIVE EXAMPLE 2

The pulp exposure cavity group for Comparative Example (the fine particles of a hydrolyzed ethylene-vinyl acetate copolymer in which collagen is immobilized was not added and only an adhesive was used in Example 4) was evaluated and, as a result, it was confirmed that the thickness of the regenerated dentin layer was 360 µm, but inflammation was observed at the dental pulp portions.

EXAMPLE 5

Evaluation was carried out in the same manner except that the fine particles containing a hydrolyzed ethylene-vinyl acetate copolymer having an ethylene amount of 29% by mol, a hydrolysis degree of 99.7% by mol and an average polymerization degree of 450 and the addition amount of boric acid of 0.03 part were used in Example 4. As a result, inflammation was hardly observed at the dental pulp portions of the pulp exposure cavity group for Example and the thickness of the regenerated dentin layer was 520 µm.

Further, the introduction amount of a carboxyl group was 1.30 µmol·cm$^{-2}$ and the immobilization amount of collagen was 30 µg·cm$^{-2}$ at this time.

EXAMPLE 6

Evaluation was carried out in the same manner except that the fine particles containing a hydrolyzed ethylene-vinyl acetate copolymer having an ethylene amount of 29% by mol, a hydrolysis degree of 99.7% by mol and an average polymerization degree of 450 and the addition amount of boric acid of 0.03 part by weight were used and the addition amount of the fine particles was 20 parts in Example 4. As a result, inflammation was hardly observed at the dental pulp portions of the pulp exposure cavity group for Example and the thickness of the regenerated dentin layer was 550 µm.

INDUSTRIAL APPLICABILITY

Since the dental material primer and dentin-regenerating pulp-capping agent of the present invention contain the hydrolyzed ethylene-vinyl acetate copolymer in which collagen is immobilized, they exhibit an excellent dentin regeneration action and are very useful for a biologically direct pulp-capping method in dental treatment.

The invention claimed is:

1. A dental material primer comprising a hydrolyzed ethylene-vinyl acetate copolymer in which collagen is immobilized, and a hydroxyl group-containing polymerizable monomer or an acidic group-containing polymerizable monomer as a primer component;
   wherein the hydrolyzed ethylene-vinyl acetate copolymer, in which collagen is immobilized, is fine particles having an average particle size of 0.2 µm to 30 µm;
   wherein the amount of the hydrolyzed ethylene-vinyl acetate copolymer, in which collagen is immobilized, is 1 to 50% by weight; and
   wherein the dental material primer contains a boron compound in an amount of 0.001 to 0.1 part by weight converted to boron content based on 100 parts by weight of the hydrolyzed ethylene-vinyl acetate copolymer, in which collagen is immobilized.

2. A dentin-regenerating pulp-capping agent comprising a hydrolyzed ethylene-vinyl acetate copolymer in which collagen is immobilized, and a binder;
   wherein the hydrolyzed ethylene-vinyl acetate copolymer, in which collagen is immobilized, is fine particles having an average particle size of 0.2 µm to 30 µm; and
   wherein the dentin-regenerating pulp-capping agent contains 1 to 100 parts by weight of the hydrolyzed ethylene-vinyl acetate copolymer, in which collagen is immobilized, based on 100 parts by weight of the binder, and contains a boron compound in an amount of 0.001 to 0.1 part by weight converted to boron content based on 100 parts by weight of the hydrolyzed ethylene-vinyl acetate copolymer, in which collagen immobilized.

3. The dentin-regenerating pulp-capping agent of claim 2, wherein the binder comprises a photo-curable monomer.

4. The dental material primer comprising a hydrolyzed ethylene-vinyl acetate copolymer in which collagen is immobilized, and a hydroxyl group-containing polymerizable monomer or an acidic group-containing polymerizable monomer as a primer component;
   wherein the hydrolyzed ethylene-vinyl acetate copolymer, in which collagen is immobilized, is fine particles having an average particle size of 0.2 µm to 30 µm; and
   wherein the dental material primer contains a boron compound in an amount of 0.001 to 0.1 part by weight converted to boron content based on 100 parts by weight of the hydrolyzed ethylene-vinyl acetate copolymer, in which collagen is immobilized.

5. A dentin-regenerating pulp-capping agent comprising a hydrolyzed ethylene-vinyl acetate copolymer in which collagen is immobilized, and a binder;
   wherein the hydrolyzed ethylene-vinyl acetate copolymer, in which collagen is immobilized, is fine particles having an average particle size of 0.2 µm to 30 µm; and
   wherein the dentin-regenerating pulp-capping agent contains a boron compound in an amount of 0.001 to 0.1 part by weight converted to boron content based on 100 parts by weight of the hydrolyzed ethylene-vinyl acetate copolymer, in which collagen is immobilized.

6. A dentin-regenerating pulp-capping agent comprising a hydrolyzed ethylene-vinyl acetate copolymer in which collagen is immobilized, and a binder; and
   wherein the dentin-regenerating pulp-capping agent contains a boron compound in an amount of 0.001 to 0.1 part by weight converted to boron content based on 100 parts by weight of the hydrolyzed ethylene-vinyl acetate copolymer, in which collagen is immobilized.

7. A dental material primer comprising a hydrolyzed ethylene-vinyl acetate copolymer in which collagen is immobilized, and a hydroxyl group-containing polymerizable monomer or an acidic group-containing polymerizable monomer as a primer component;
   wherein the primer has the property that when the primer is applied to a pulp exposed dental cavity, the primer regenerates dentin with no or hardly observable inflammation at dental pulp portions of the cavity; and
   wherein the immobilization amount of collagen in the hydrolyzed ethylene-vinyl acetate copolymer is at least 5 µg·cm$^{-2}$ and no more than about 40 µg·cm$^{-2}$.

8. A dentin-regenerating pulp-capping agent comprising a hydrolyzed ethylene-vinyl acetate copolymer in which collagen is immobilized, and a binder;

wherein the agent has the property that when the agent is applied to a pulp exposed dental cavity, the agent regenerates dentin with no or hardly observable inflammation at dental pulp portions of the cavity; and wherein the immobilization amount of collagen in the hydrolyzed ethylene-vinyl acetate copolymer is at least 5 µg·cm$^{-2}$ and no more than about 40 µg·cm$^{-2}$.

* * * * *